(12) United States Patent
Mullen et al.

(10) Patent No.: US 7,774,211 B1
(45) Date of Patent: Aug. 10, 2010

(54) METHOD AND SYSTEM FOR GRAPHICALLY DISPLAYING CONSOLIDATED CONDITION DATA FOR EQUIPMENT IN A HOST FACILITY

(75) Inventors: Paul L. Mullen, Waukesha, WI (US); Mobit S Kathuria, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 2497 days.

(21) Appl. No.: 09/681,475

(22) Filed: Apr. 13, 2001

(51) Int. Cl.
*G06Q 10/00* (2006.01)
(52) U.S. Cl. .......................................... 705/2
(58) Field of Classification Search ................... 705/28, 705/29, 22, 30, 2
See application file for complete search history.

(56) References Cited

U.S. PATENT DOCUMENTS

| | | | | |
|---|---|---|---|---|
| 5,610,811 A | * | 3/1997 | Honda | 705/2 |
| 5,732,401 A | * | 3/1998 | Conway | 705/29 |
| 5,996,889 A | * | 12/1999 | Fuchs et al. | 235/375 |
| 6,085,493 A | * | 7/2000 | DeBusk et al. | 53/445 |
| 6,175,934 B1 | * | 1/2001 | Hershey et al. | 714/25 |
| 6,182,249 B1 | * | 1/2001 | Wookey et al. | 714/47 |
| 6,237,114 B1 | * | 5/2001 | Wookey et al. | 714/47 |
| 6,272,493 B1 | * | 8/2001 | Pasquali | 707/10 |
| 6,317,639 B1 | * | 11/2001 | Hansen | 700/83 |
| 6,338,045 B1 | * | 1/2002 | Pappas | 705/29 |
| 6,338,152 B1 | * | 1/2002 | Fera et al. | 714/48 |
| 6,385,593 B2 | * | 5/2002 | Linberg | 705/28 |
| 6,640,239 B1 | * | 10/2003 | Gidwani | 709/203 |
| 6,651,190 B1 | * | 11/2003 | Worley et al. | 714/43 |
| 6,668,203 B1 | * | 12/2003 | Cook et al. | 700/65 |
| 6,738,748 B2 | * | 5/2004 | Wetzer | 705/9 |
| 2002/0116541 A1 | * | 8/2002 | Parker et al. | 709/318 |

* cited by examiner

*Primary Examiner*—Ronald Laneau
(74) *Attorney, Agent, or Firm*—Ziolkowski Patent Solutions Group, SC (57) ABSTRACT

A system and process to manage and administer assets of an institution is provided and includes a graphical user interface to display urgent device alerts and scheduled tasks reminders. The system includes a consolidation engine that, at a centralized processing facility, receives and consolidates data from a number of auto-generation and manual-generated data sources, which are located within a host facility. A method to graphically display consolidated condition data for equipment of a host facility is also provided.

27 Claims, 6 Drawing Sheets

METHOD AND SYSTEM FOR GRAPHICALLY DISPLAYING CONSOLIDATED CONDITION DATA FOR EQUIPMENT IN A HOST FACILITY

BACKGROUND OF INVENTION

The present invention relates generally to equipment monitoring and administration and, more particularly, to a method and system of graphically displaying consolidated condition data for equipment of a host facility.

In a fast paced, ever changing, complex marketplace it is incumbent upon administration managers and personnel to actively, if not continually, monitor the operating condition of a company's or facility's assets. It is not only imperative that administrators maintain a close watch of asset operating condition, i.e., devices in need of repair, but administration officials must also be aware of asset location within a given facility. Without an aggressive monitoring and management program, the efficiency as well as the efficacy of the work of a particular business or enterprise is jeopardized. Further, failure to maintain assets or devices in a proper and timely fashion may result in undue harm to the users of the devices.

For example, hospital administrators must actively monitor the condition and location of medical devices throughout the hospital facility. The task of actively monitoring the devices has become, in recent years, much more difficult as hospital facilities have grown and/or consolidated. To properly monitor the devices, the hospital administrators must rely on feedback from various employees and service technicians to keep a watchful eye on device operating conditions. Further, known administration systems require the generation of several condition reports from various officials throughout the hospital facility to determine if a particular device is in need of immediate repair or servicing, or if device servicing is or should be scheduled. In a complex hospital facility having hundreds of medical devices, such as, magnetic resonance imaging systems, computed tomography systems, nuclear medical imaging systems, defibulators, pumps, x-ray devices, etc., it is paramount that the administration officials aggressively monitor device location and/or operational status. That is, hospital administrators should be reminded, in real-time, if a particular device is scheduled for servicing as well as be alerted if a particular device is presently located in an authorized area or suffered a particular breakdown in operation, i.e., unexpected power failure. With aggressive monitoring and management of the various devices, hospital officials are able to reasonably detect and eliminate improper device operation and unauthorized device positioning.

Further, known administration systems provide often voluminous status reports and scheduling reports to hospital officials detailing device alerts and/or reminders. Even with a nominally sized facility, accumulation, consolidation, and interpretation of these documents can be time-consuming, inefficient, and ultimately ineffective for adequately ensuring proper device operation.

It would therefore be desirable to design a system for providing real-time condition data in a single interface thereby enabling hospital officials to reasonably determine present device alerts and future reminders of device servicing.

SUMMARY OF INVENTION

A system and method of graphically displaying in real-time status information for a plurality of devices in a host facility are provided overcoming the aforementioned drawbacks.

In accordance with one aspect of the present invention, a method for remotely managing a medical institution is provided. The method includes the steps of remotely collecting condition data representative of device status for a number of devices utilized in the medical institution. The condition data includes device diagnostic data as well as device reminder data. The method continues with storing the condition data on a database at a centralized facility and reviewing the condition data to identify at least the device diagnostic data and the device reminder data. The method further includes the step of displaying on a graphical user interface the device diagnostic data and the device reminder data.

In another aspect of the present invention, a graphical user interface (GUI) is provided to display management information for a plurality of devices of a remotely located host. The GUI is configured to include a number of alert indicators that are designed to indicate device urgencies and a number of reminder indicators configured to display scheduled items relating to a particular device. The GUI also includes a number of general information textlinks configured to display general information regarding a device including device updates, device technology news, as well as, information pertaining to the host facility.

In yet a further aspect of the present invention, a system to display consolidation information for remote facility comprises a computerized network, a readable memory electronically linked to the network, and a plurality of computers connected to the network wherein at least one of the plurality of computers displays electronic data to a user in the form of a graphical user interface. The system also includes a processing unit capable of calling a GUI on demand and causing a representation of condition data to be displayed upon request by the user. The system further includes a plurality of devices connected to a consolidation facility and a computer at the consolidation facility programmed to continually acquire condition data of a plurality of devices. The computer is further programmed to continually acquire reminder data wherein the reminder data includes a plurality of scheduled tasks and display the condition data and the reminder data on a refreshable GUI.

In a further aspect of the present invention, a computer data signal is provided and embodied in a carrier wave and representing a sequence of instructions that when executed by one or more computers causes the one or more computers to acquire automatically generated data from a number of auto generation data sources of the remote facility. The sequence of instructions further causes the one or more computers to acquire manually entered data from a number of manual generation data sources located within the facility. At a centralized processing station, the automatically generated data and the manually entered data previously acquired are consolidated and displayed on a GUI wherein the GUI is accessible from the remote facility.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention. In the drawings.

DETAILED DESCRIPTION

The present invention will be described with particular reference to the consolidation of device status information for a plurality of devices of a medical institution. One of ordinary skill in the art will appreciate, however, that the present invention is not limited to implementation within a medical facility, but is also applicable to other facilities having equipment that administrative officials seek to aggressively monitor, maintain, and perform preventive maintenance thereto. For example, the present invention may be implemented in a manufacturing setting to maintain proactive review of manufacturing machines and/or processes as well as office environments wherein department managers may monitor office equipment such as computers, copiers, portable devices, and the like.

Figure 1:
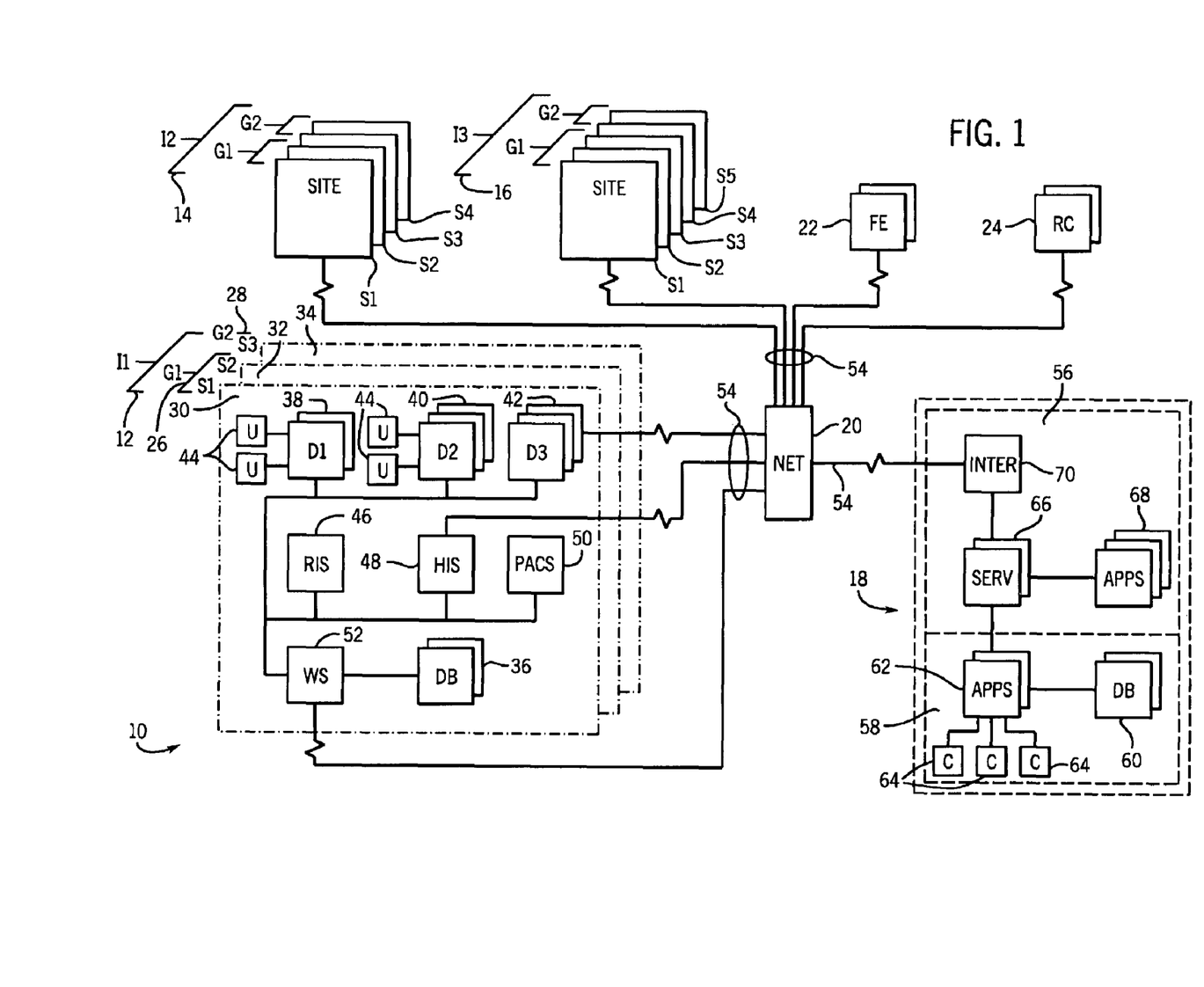
FIG. 1 is a schematic block diagram of a service system for collecting and analyzing data for one or more medical institutions.

Referring to FIG. 1, a service system 10 is represented for monitoring, data collection, data analysis, and reporting relating to medical equipment in one or more medical institutions. As illustrated, system 10 includes a plurality of institutions 12, 14 and 16, details of which are represented only for the first institution 12. In accordance with aspects of the present technique, any number of institutions may be serviced by a topography such as that illustrated in FIG. 1, or various modified topographies employing the techniques described below. System 10 further includes at least one service provider 18 which services the medical equipment of the institutions, collects and analyzes data on the equipment, and provides reports relating to the equipment inventory, performance, and so forth. In the illustrated embodiment, the institutions and the service provider may be linked via a network 20, such as the Internet, an intranet, a private dial-up system, or any other communication link. In a general implementation, the system may also permit access of data records by field engineers or technicians 22, and by remote clients 24. The field engineers and remote clients may, where appropriate, access or input data via mobile computer systems, remote computer terminals, and so forth.

Within each institution, a variety of functional portions or subdivisions may be defined, and data collected and analyzed in accordance with such functional portions. In the embodiment of FIG. 1, for example, institution 12 includes two functional groups 26 and 28, and three facility sites 30, 32 and 34. Sites 30 and 32 comprise group 26, while site 34 forms group 28. As will be described below, the present technique facilitates a collection and centralized storage of medical equipment data for individual sites, individual departments within the sites, institutions, and logical groupings. By way of example, where an institution includes sites in geographically dispersed locations, each site may be accounted for separately, but with the equipment data being referenced by site and institution, permitting an overview by either the site or the institution. Similarly, logical groupings, such as by political subdivisions (e.g., state, country, city) or fiscal or taxing jurisdictions may be specified and the data accordingly referenced.

Within each site, a variety of departments and systems may be designated and interfaced with one another. A centralized database 36 is compiled including data relating to medical equipment maintained (e.g., owned, managed, leased) by the institution. It should be noted that the database could be stored on any suitable memory device, and/or multiple memory devices, as shown, may be provided for storage of all or part of the database, or to provide backup and redundancy in storage. In general, however, the centralized database forms, for the user, a central repository for medical equipment data which can be accessed, processed, transferred, stored, and maintained to facilitate the tracking, management, planning, and other decision-making.

In the embodiment of FIG. 1, institution 12, at site 30, includes a variety of departments 38, 40 and 42. Depending upon the mission of the institution, these departments may include radiology departments, emergency care facilities, neonatal care facilities, oncology units, and so forth. Within each department, medical equipment is maintained for providing medical care to patients. In the present context, the medical equipment may include a wide range of disposable and non-disposable resources, such as patient monitors, input and readout devices, and so on. Generally, however, the medical equipment may also include elements of the physical plant of the institution, including beds, wheelchairs, computer systems, and so forth. In certain departments the equipment may further include imaging stations, scanners, probes, coil assemblies, and so forth. The equipment of each department is available for operation by nurses, clinicians, physicians, and other users, as indicated diagrammatically by reference numeral 44 in FIG. 1.

In addition to the medical equipment assigned to each department, the institution may include additional systems which are interfaced in the institution information system. For example, a radiology department information system (RIS) 46, a hospital information system (HIS) 48, a picture archiving and communication system (PACS) 50, and other similar information management systems may be provided. One or more management stations, such as a conventional computer workstation 52, is provided, preferably at each site, for reviewing reports and data generated as described below. It should be noted that a variety of such management stations may be provided, including fully or partially enabled management stations within each department. Various departments and systems within the institution will be provided with configurable network interfaces, such as modems or other network connections, so as to facilitate transmission and reception of data via network links 54 and network 20.

Service provider 18, which may function partially within the institution itself, includes processing capabilities for accessing, analyzing and reporting on data collected by the institutions on the medical equipment. It should be noted, however, that in the embodiment illustrated in FIG. 1, the service provider 18 may maintain facilities remote from one or more of the institutions and one or more of the facility sites, with data being transmitted between the institutions and the service providers via network 20. In the embodiment illustrated in FIG. 1, service provider 18 includes processing capabilities divided into a first processing space 56 and a second processing space 58. As described below, to maintain heightened security for data stored by the service provider, processing space 58 may be separated from space 56 to substantially limit access to processing space 58 from users outside the service provider system. In the present context, space 58 serves to store medical equipment records, to process data from the records, and exports data files for generation of reports within processing space 56. Thus, one or more databases 60 are maintained by the service provider 18, with processing capabilities in a form of specific applications 62 provided for storing, associating, analyzing, and extracting data from the database. Clients 64 may access the applications for performing the data manipulation functions at the service provider. One or more servers 66 are linked to the applications 62 to receive data files used as the basis for generating equipment reports. Additional applications 68 serve to format and process the reports. Finally, a network interface 70 is provided, such as including a router, modems, or similar network interface circuitry, for receiving data and transmitting data and reports to the medical institutions from the service provider.

Figure 2:
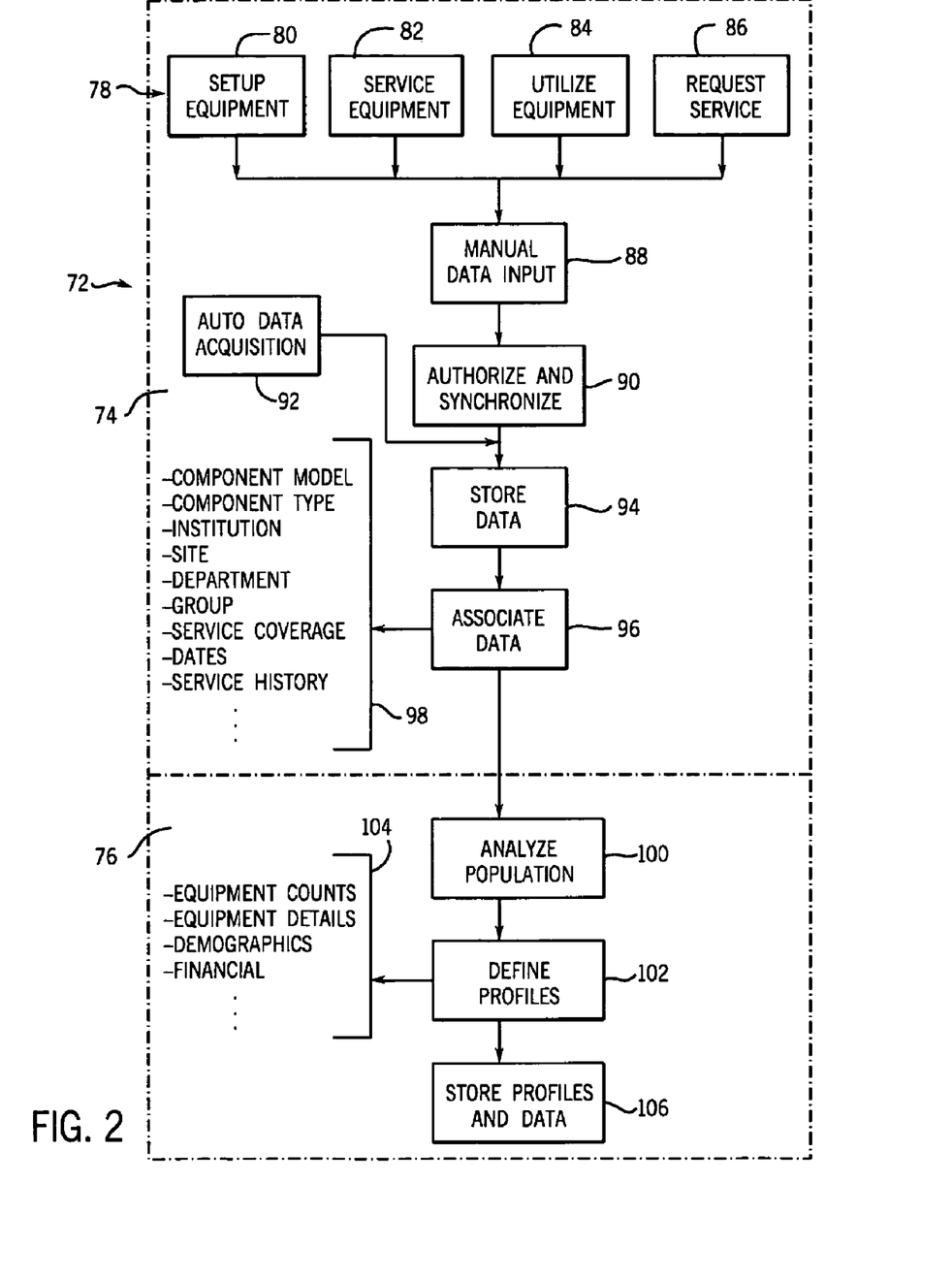
FIG. 2 is a flow chart representing exemplary control logic for collecting and analyzing the data of the type illustrated in FIG. 1.

FIG. 2 represents exemplary logic for accessing or collecting, storing, and analyzing medical equipment data in a system of the type illustrated in FIG. 1. The processing illustrated in FIG. 2 may be logically subdivided into a data collection/storage/association sequence 74, and a population data analysis sequence 76. Within the sequence 74, data is collected for medical equipment within departments, sites, groups and institutions either manually, as indicated at reference numeral 78, or by automatic acquisition. Any suitable data input technique may be employed, typically including manual input via a workstation, laptop computer, handheld device, and so forth. Thus, as illustrated in FIG. 2, input may be by equipment setup upon its initialization, as indicated at reference numeral 80, or by subsequent servicing (i.e., as individual equipment components are serviced) as indicated at reference numeral 82. Other data may be manually input as the equipment components are utilized as indicated at 84, or upon specific service requests as indicated at reference numeral 86. At any one of these or other points in the operation of the medical equipment, the data relating to the equipment is thus manually input as indicated at reference numeral 88. To limit access to the data input system, and to maintain the integrity of the data, an authorization and synchronization sequence 90 is preferably implemented, such as through password protection, permitting authorized personnel only or authorized stations to input equipment data. Synchronization is performed to maintain up-to-date equipment data once the input is performed.

As an alternative to manual data input, certain automatic data acquisition may be performed as indicated at reference numeral 92 in FIG. 2. Automatic data acquisition may include polling of certain equipment, such as at regular intervals or according to a regular schedule. Networked equipment may thus be tracked and its performance monitored through data stored at the equipment and transmitted at step 92. Following either step 90 or 92, the data is stored as indicated at reference numeral 94. As noted above, the data may be stored at one or more storage devices, but with the data being associated in a centralized database for the institution. Again, the centralized database may be located physically at one or more of the institution sites, or off-site, such as at a location of the service provider 18.

At step 96, the data collected for the medical equipment is associated in the centralized database in accordance with any number of logical references. The data itself preferably includes references which facilitate or comprise the association as indicated at reference numeral 98. Thus, the component data may include both the identification of the component, the component model, including its manufacturer and model designation, and a component type, typically indicated by the function of the equipment. The data also preferably includes a reference representative of the institution, the site at which the components are located, the departments to which the components are assigned, if assigned, and the group designation for associating the departments or sites logically. The service data for each component also preferably includes a reference to service agreements or contracts for all or partial coverage of the components, including original warranty data and after-purchase service contracts or subscriptions. Relevant dates are preferably included, such as the date of purchase or entry into service, dates of servicing, and expiration or renewal dates for service arrangement coverage. Moreover, specific service history information may be included, where individual components have been regularly serviced or serviced on an as-needed basis. Such service history data may also include error codes, service request records input by the institution or users, breakdown records, downtime records, subcomponent replacement records, and so forth.

The population data analysis sequence 76 permits benchmarking or profiling of specific institutions and groups of institutions in accordance with equipment usage characteristics and other considerations. Where the service provider has access to equipment records for a range of institutions, the records are preferably analyzed to identify commonalities between the institutions, sites, departments, and groups. Such analysis may include consideration of the types of institutions, the types of departments, the types of equipment utilized, and the utilization characteristics (e.g., number of components, duty imposed on components, replacement or service records, and so forth). Based upon the analysis, characteristic profiles are identified which correspond to typical institutions, sites, departments, or groups that may be used as a basis for comparing a particular institution by equipment inventory and utilization for benchmarking purposes. It should be noted that benchmarking analysis preferably results in profiles which do not identify any individual institution, but which identify only a larger groups of institutions (such as groups of 20 or more) considered representative of a particular profile. The profiles, defined at step 102, may thus include reference data 104 such as equipment counts, equipment details, demographics, and financial profiles. At step 106 the profiles and corresponding reference data are stored, preferably in the database for the service provider, for future reference in benchmarking and service planning as described below.

Figure 3:
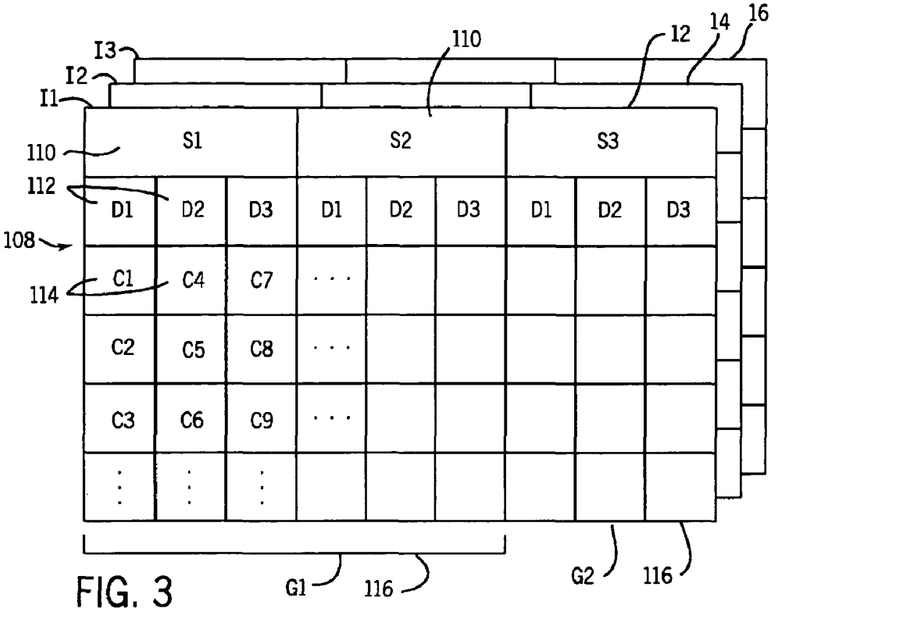
FIG. 3 is a diagrammatical representation of data records including data associated with institutions, sites, departments, groups, and components collected and processed in accordance with the aspects of the present invention.

The medical equipment records stored in the centralized database thus form a dataset or structure which permits and facilitates analysis by institution, site, department, group, component, component type, and other reference features. The database records may be considered to form a multi-dimensional data matrix structure which inter-relates these various aspects of the equipment component data as illustrated in FIG. 3. As shown in FIG. 3, the data record 108 for an institution 12 may thus include references 110 to specific facility sites at which equipment components are located. Additional departmental records 112 specify the department to which equipment components are assigned. Records for each department and site are then maintained for each component at reference numeral 114, including the identification and service information of the type described above. Moreover, the site, department, and component records may be associated by group designations 116. Where additional institutional records are available to the service provider, these may form a similar databases as illustrated in FIG. 3, permitting the analysis of groups of institutions to establish the profiles mentioned above.

Figure 4:
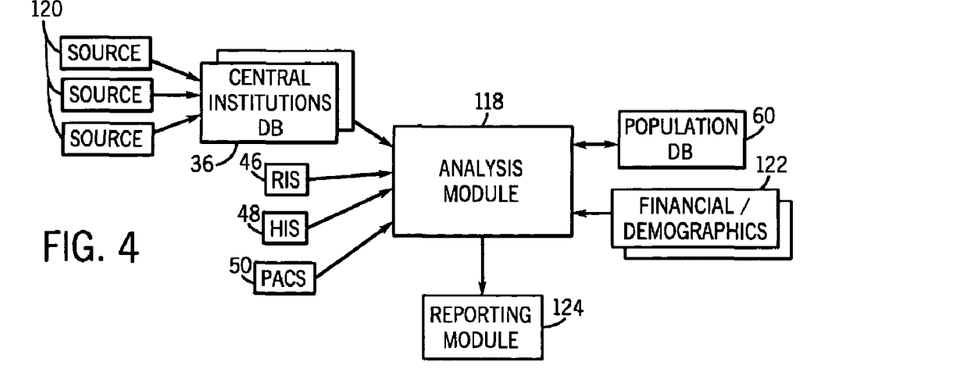
FIG. 4 is a data flow diagram illustrating the multiple sources of data utilized in analysis and reporting of institutional biomedical equipment data.

It should be noted that the present technique provides not only a centralized database for maintaining medical institution equipment records, but integrates a wide range of informational sources both at the institution and sources available to a service provider. FIG. 4 illustrates diagrammatically an example of the types of information sources which are integrated through the present technique. As described below, an analysis module 118 is provided either at the institution, or preferably at the service provider for accessing and analyzing the equipment records. The analysis module may incorporate a range of analysis algorithms, search techniques, and software applications, for deriving useful management data from the component records. In a general sense, the analysis module performs counts, statistical analysis, and associations of the equipment components by site, department, institution, group and manufacturer, as well as by any other references provided in the component records. The analysis module draws such information from the institutional database 36, as well as from other information systems of the institution, such as the RIS 46, the HIS 48, any PACS 50 present in the institution, or other institutional information systems. Again, the central institution database 36 may, in turn, obtain information from various sources, designated generally by reference numeral 120 in FIG. 4, such as departmental data entry systems, stationary or mobile data input devices, field engineer or service personnel laptops, and so forth. Similarly, analysis module 118 accesses information from population databases 60, such as for comparison in benchmarking, as well as financial, demographics, and other input 122, which may include publicly available sources, such as searchable databases, industry-specific databases, and so forth. Based upon analysis performed by the analysis module 118, a reporting module 124 is provided for generating and delivering reports representative the component records, and analysis derived from the component records.

Figure 5:
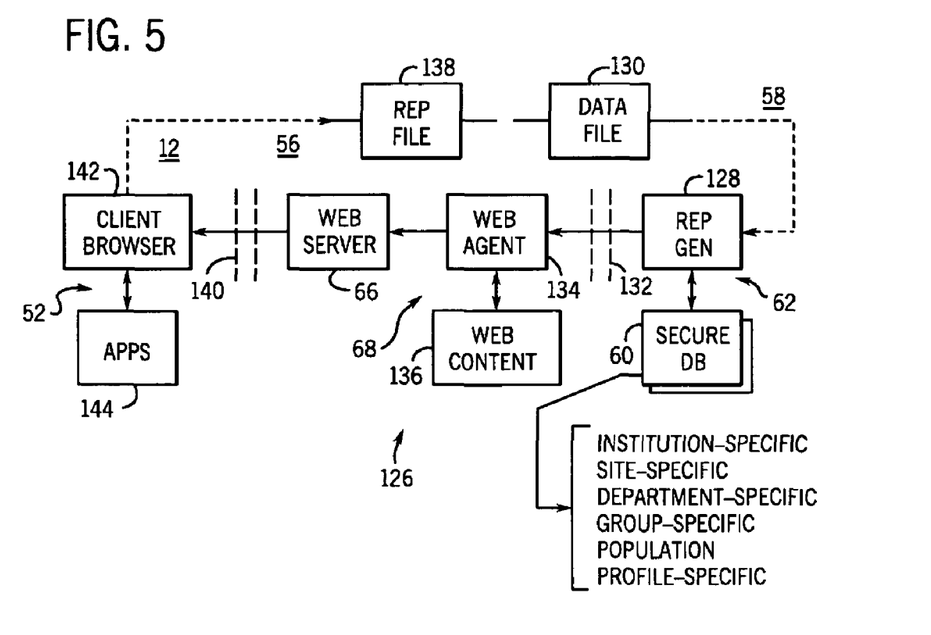
FIG. 5 is a work flow diagram illustrating functional components for securely generating reports based upon collected equipment data and for delivering the reports to a medical institution.

FIG. 5 is a diagrammatical representation of reporting workflow, designated generally by reference numeral 126, for operation of the analysis and reporting modules of FIG. 4. As shown in FIG. 5, the service provider secure database 60 is maintained in the secure processing space 58. Among the software applications 62 operative in the secure processing space 58, is a report generation application 128, which forms part of the reporting module represented generally at reference numeral 124 in FIG. 4. On a periodic basis, or upon request, the report generation application 128 accesses the data record 108 (see, e.g. FIG. 3) for the institution, and calculates or derives any inter-related data not already contained in the record for use in a management report or reports to be transmitted to the medical institution. In the example illustrated in FIG. 5, the data record includes information which institution-specific, site-specific, department-specific and group-specific. Moreover, database 60 may also include a data representative of known populations of medical institutions, sites, groups, or components, as well as pre-calculated data which is profile-specific. As noted above, the profiles generated based upon known population data may categorize institutions and other logical groupings by size, demographics, and so forth. Report generation application 128 produces a data file 130 containing data or fields of data, which is then exported via a firewall 132 to processing space 56.

Within processing space 56 additional hardware and software components are provided for translating the data file 130 into one or more report files. Thus, in the illustrated embodiment, applications 68 within the processing space 56 include a web agent 134 which is adapted to place data from file 130 into a predefined report template. Other web content, and input for generating the report is provided in one or more files 136. By integrating the data file and web content in the predefined report template, a report file 138 is generated, which may be adapted for presentation in any suitable manner, such as an HTML page in a conventional web browser. The report file 138 is then stored and is available for distribution via a web server 66.

In a present implementation, the web server 66 transmits the report file 138 via a configurable network link, such as the Internet, and through a firewall 140. At the medical institution 12, and typically at a management station 52, a client browser application 142 facilitates viewing and navigating through various portions of the report as described more fully below. Additional applications 144 may be available for manipulation of the report, formatting of the report, printing of hard copies and so forth.

The present invention contemplates a system whereby department administrators may effectively and efficiently monitor and administer devices or other assets of their departments. The present invention further contemplates real-time administrative oversight of dispatching and incident tracking systems, billing, invoicing and contract management systems, as well as, news feed, and Internet search engines. In further embodiments, the present invention enables the administrators to recall marketing messages, messages from field personnel, such as, sales representatives and field service engineers, and customer generated information and messages.

Figure 6:
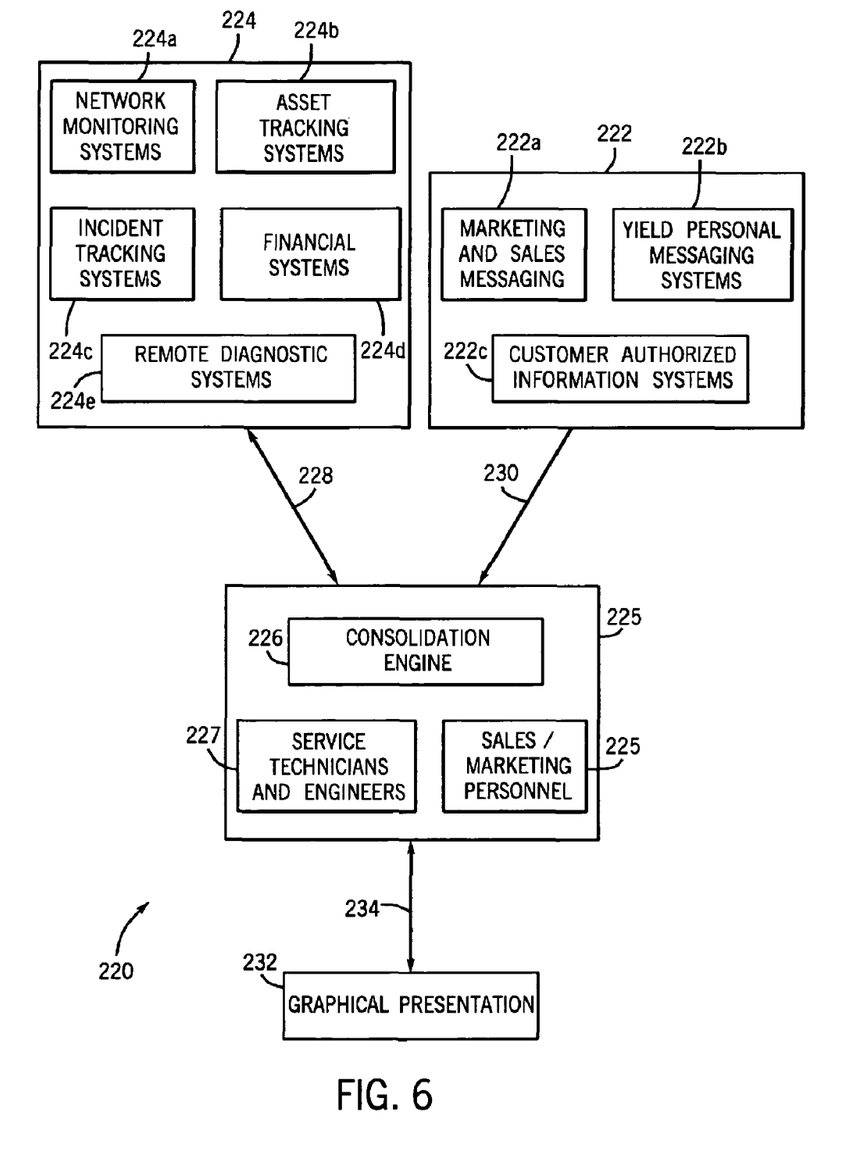
FIG. 6 is a schematic block diagram representing the consolidation of automatically generated and manually generated information in accordance with the present invention.

Now referring to FIG. 6, a schematic block diagram illustrates the acquisition and consolidation of data for presentation to a facility administrator or other user via a graphical user interface (GUI), such as, an Internet-based web page. As shown in FIG. 6, a consolidation system 220 consolidates manually entered data 222 as well as automatically generated information 224 in a single consolidation engine 226 housed in a remote processing facility 225. In a preferred embodiment, the consolidation engine receives the auto generation data and the manual generation data 222, 224 via a secure, high-speed communication interface 228. Alternatively, however, the auto-generated data 224 and the manually-generated data 222 may be transmitted to the consolidation engine 226 through an Internet, direct dial-up, LAN, WAN, wireless, or other public or private communication system.

The present invention contemplates the receipt of automatically generated data from a number of information providing resources, those information providing resources include network monitoring systems 224a, dynamic assets tracking systems 224b, and dispatching an incident tracking systems 224c. Other auto-generation systems such as billing, invoicing, and contract management systems 224d as well as remote monitoring and diagnostic systems 224e, such as, the GE Insite® Remote Monitoring Systems are also contemplated. The foregoing list is merely indicative of the various auto generation sources that are applicable with the present invention, but the aforementioned enumeration is certainly not exhaustive. A number of manual generation information sources are contemplated for use with the present invention. The manual generation sources include, but are certainly not limited to, marketing messaging systems 222a, field personnel messaging systems 222b, such as paging and telephone systems, as well as customer-entered information systems 222c. Again, the aforementioned list is provided to illustrate the types of manual generation information sources applicable to the present invention, but is not exhaustive of the applications for which the present invention may be utilized.

Still referring to FIG. 6, consolidation engine 226 receives data information from data sources 222, 224 via communication links 230, 228, respectively. It should be noted however, that communication link 228 is bi-directional, thereby, allowing the consolidation engine to not only receive information from the auto generation data sources 224, but also provide information to the auto-generation data sources 224. That is, the consolidation engine 226 may transmit across communication line 228 to an auto-generation data source 224 in response to the receipt of manual entered data information 222 via communication link 230.

The consolidation engine 226 generates a graphical representation 232 configured to include the consolidated auto-generation and manually-entered data. In a preferred embodiment, the graphical presentation 232 includes a graphical user interface or web page to display the consolidated information. Further, the consolidation engine 226 transmits the consolidated data for the graphical presentation via an Internet connection 234. It is understood, however, that other communication systems such as WAN, LAN, cable, T1-T3, satellite, direct dial-up, or wireless platforms may be employed singly or in combination to transmit the consolidated information from the consolidation engine 226 to the graphical presentation 232.

The present invention contemplates a management system wherein the consolidation engine 226 is located and maintained at a centralized facility 225 remote from the medical institution housing the auto-generation and manual-generation data resources 224a, 224e, 222a, 222c. That is, the present invention contemplates the consolidation engine 226 acquiring data from medical devices and other diagnostic systems remotely and consolidating the received information at a centralized processing facility. After the information is consolidated at the centralized processing facility, the information is displayed on a GUI or web page that may be accessed by administration personnel located at the medical institution. Further, housing the consolidation engine within the centralized yet remote facility information authored by individuals within the remote facility, such as, service technicians and/or engineers 227 and marketing/sales personnel 229, may be incorporated and consolidated with the auto-generation and manually-entered data received from the remote medical institution. As a result, service technicians and/or engineers affiliated with the centralized processing facility may efficiently and effectively provide alert or reminder information, such as, product updates or product "bugs" to department administration officials.

Figure 7:
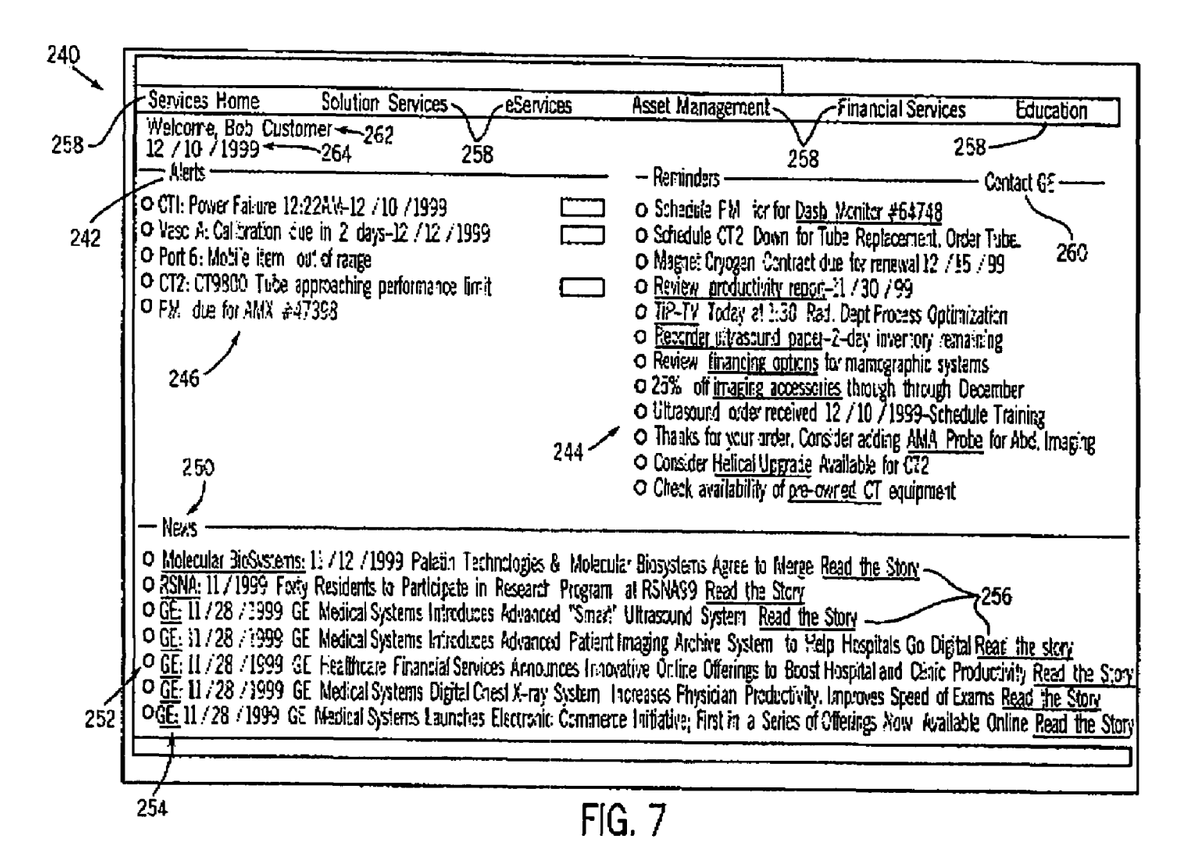
FIG. 7 is a representation of a graphical user interface configured to display consolidated information in accordance with the present invention.

To display consolidated information for a number of hospital systems, such as, remote monitoring and diagnostic systems, asset tracking systems, and incident tracking systems, as well as messaging systems, the present invention contemplates a web-based, Internet available GUI as shown in FIG. 7. Shown is a GUI 240 displaying consolidated device management information. For example, GUI 240 succinctly displays device servicing information. In one embodiment, the servicing information is grouped in an "Alerts" 242 and a "Reminders" 244 arrangement. The Alerts grouping 242 includes a number of servicing items and/or tasks requiring urgent attention 46. For example, an urgent servicing item might include an indication that a particular device of the medical institution suffered a power failure or an indication that a particular mobile item is out of its allowable range. Additional Alerts could include that a device calibration to ensure proper functioning is required immediately or that a particular device is approaching its performance limit or that a preventive maintenance schedule date has lapsed.

The "Reminders" group 244, in this embodiment, details reminders of scheduled tasks for hospital administration personnel pertaining to one or more of the institutions devices. For example, a reminder item might include a reminder that a particular device is scheduled for preventive maintenance, periodic shutdown, part replacement, or general servicing needs. Further reminders might include reminders that upgrades to a particular option in a device are available, training for a newly received device or activated option has been scheduled and upcoming, or supplies associated with a particular device, such as, imaging paper has a low inventory level and is in need of reordering.

The above arrangement of Alert 242 and Reminder 244 data on GUI 240 illustrates one embodiment of the present invention. It is understood, that additional arrangements with different substantive concerns are contemplated and within the scope of the present invention. That is, differing institutions and/or facilities will have differing needs and the present invention includes the flexibility to adjust GUI 40 to serve those differing needs.

Still referring to FIG. 7, GUI 240, in a preferred embodiment, includes a "News" group 250. News group 250 includes a listing of a number of newsworthy items 252 that may be of interest to a viewer of GUI 240. The newsworthy items 252 might include medical institution related press releases, customer related newsworthy items, and/or product supplier press releases, such as, the availability of product upgrades, announcements regarding training seminars, or the introduction of new products to the market place. The present invention contemplates the inclusion of a hyperlink 254 for appropriate news items 252 that allow a user upon proper selection (mouse or pointer clicking) to link to a new navigational interface system proprietary to a particular company and/or institution. Further, the present invention contemplates a story-specific hyperlink 256 which allows the user, if he or she desires, to access a more in-depth recitation of the newsworthy item 252. Therefore, the user may access a newspaper or journal article that is summarized by the newsworthy item 252.

GUI 240 further includes a number of navigational tabs 258 that enable the user to link to additional GUIs of a navigational interface system. The navigational tabs include a "Services Home" tab, a "Solution Services" tab, an "E-Services" tab, an "Asset Management" tab, a "Financial Services" tab, and an "Education" navigational tab. These additional navigational tabs 258 allow the user to access GUIs detailing additional services provided by a business or enterprise associated with the centralized facility 225, FIG. 6. GUI 240 further includes a "Contact" tab 260 wherein a user upon selection may access an electronic messaging system and/or subsequent GUI configured to provide contact information, such as, email addresses, toll-free telephone numbers, fax numbers, business addresses, and mail receiving addresses for the servicing enterprise.

Since an institution, such as, a hospital, may have several department officials responsible for maintenance and management of institution devices and/or assets, the present invention contemplates configuring GUI 240 to be specific to a particular administrator or resource manager. Customizing GUI 240 to be specific to a particular administrator has several advantages. For example, through customization, the hospital administrator or resource manager is not required to sift through a number of Alerts and/or Reminders to determine those for which he or she is responsible. As such, differing reports need not be generated for different administration officials. Furthermore, a customized GUI 240 allows the institution to maintain a sense of privacy as to what is displayed regarding asset information and to whom. For instance, a particular institution may desire to limit knowledge of a particular scheduled task or an unexpected yet urgent servicing need to a particular hospital administrator. That is, for liability and other concerns, the hospital may wish to limit awareness to its servicing and repair protocols. In light of the aforementioned, GUI 240 further includes a user identifier 262 as well as a date identifier 264. Inclusion of data identifier 264 allows the identified user 262 to "Save" GUI 240 as a document in memory of the user's computer and/or terminal. Therefore, the identified user 262 may maintain a digital record of the Alert 242, Reminder 244 and News 250 information that was displayed on GUI 240 at a given moment.

The present invention discloses an Internet-enabled department GUI for improving device management and monitoring efficiency. The present invention provides real-time presentation of device status data through the continual detection and consolidation of automatically-generated as well as manually-generated data systems. The present invention is applicable with a number of remote diagnostic and monitoring systems including those systems that provide technical, marketing, operational, and financial data. The GUI will display a consolidated information and may be personalized so that data is presented specifically to a particular user profile or role. The GUI may be personalized by a site administrator or other individual who is ultimately responsible for asset and information oversight.

Accordingly, the present invention includes a method for remotely managing a medical institution comprising the steps of remotely collecting condition data representative of device status for a number of devices utilized in the medical institution and storing the condition data on a database at a centralized facility remote from the medical institution. The condition data includes device diagnostic data as well as device reminder data. The method continues by reviewing the condition data to identify at least the device diagnostic data and the device reminder data and then displaying on a graphical user interface (GUI) the device diagnostic data and the device reminder data. The GUI is configured to automatically display updated condition data with each user refreshing or access of the GUI.

Further, the aforementioned method further includes the step of indicating on the GUI those devices requiring immediate attention including the step of identifying the devices in need of repair, servicing and updating. The method also includes the step of displaying on the GUI a Reminder profile wherein a list of devices that require routine or scheduled attention are identified. To facilitate the relaying of general but pertinent information, the method includes the step of displaying on the GUI a number of general remarks including news updates relating to the medical institution, a device supplier, or a device manufacturer. Additional newsworthy items may also be identified including those related to a particular device, a device technology, or a recent device development or device update.

The present invention contemplates the customizing of the GUI for viewing by a particular administrator, therefore, the method further includes the step of personalizing the GUI to be specific to a particular department and/or individual responsible for immediate management and monitoring of a device.

In yet a further embodiment of the present invention, a GUI for a remotely located host is provided and configured to display management information for a plurality of devices of the remotely located host. The GUI is configured to include a number of Alert indicators that identify device urgencies as well as a number of Reminder indicators configured to display scheduled items relating to a particular device. The GUI further includes a number of general information textlinks configured to display general information regarding the device including device updates, device technology news, and information pertaining to a host, such as, a medical institution or a manufacturing enterprise. The GUI is further configured to automatically display updated Alert indicators and Reminder indicators with each user access or refreshing of the GUI. For increased efficiency, the GUI is also configured to be tailored to be specific to a particular user whereby Alert indicators as well as Reminder indicators are viewable by only those persons a department administrator wishes to have access to the alert and reminding information. In a preferred embodiment, the present invention provides access to the GUI via an Internet connection.

The present invention is also directed to a system to display consolidation information for a remote facility. The system includes a computerized network, a readable memory electronically linked to the network, and a plurality of computers connected to the network wherein at least one of the plurality of computers displays electronic data to a user in the form of a graphical user interface (GUI). A processing unit is also provided and capable of calling a GUI on demand and causing a representation of condition data to be displayed upon a request by a user. To facilitate the gathering and consolidation of information, a plurality of devices are connected to a consolidation facility that houses a computer that is programmed to continually acquire condition data of the plurality of devices as well as continually acquire Reminder data wherein the Reminder data includes a plurality of scheduled tasks. The computer at the consolidation facility is also programmed to display the condition data and Reminder data on a refreshable GUI. The computer is also programmed to automatically consolidate data from a number of auto-generation systems and manual generation systems to be displayed on the GUI. Consolidating the aforementioned data, the system is able to determine those devices in need of immediate attention as well as reminding the user viewing the GUI that certain tasks pertaining to a device, although not urgent, are impending.

The present system is applicable with a myriad of auto generation and manual generation systems including remote monitoring and diagnostic systems, network monitoring systems, dynamic asset tracking systems, financial management systems, and electronic messaging systems configured to relay customer, as well as, service personnel messages.

In yet a further embodiment of the present invention, a computer data signal embodied in a carrier wave and representing a sequence of instructions that when executed by one or more computers is provided. The sequence of instructions causes the one or more computers to acquire automatically generated data from a number of auto generation data sources positioned in a remote facility as well as acquire manually entered data from a number of manual generation data sources within the remote facility. The computer data signal further causes, at a centralized processing station, the one or more computers to consolidate the automatically generated data and the manually entered data for display on a GUI that is accessible from the remote facility. Preferably, the sequence of instructions causes the one or more computers to display the GUI in an Internet accessible web page. To ensure updated and current information, the sequence of instructions further causes the one or more computers to dynamically consolidate the manually entered data and the automatically generated data thereby providing an updated display of consolidated data with each user access of the GUI. Further, the sequence of instructions further causes the one or more computers to receive data communications as the user interacts with the GUI and update the consolidated data in response to the user initiated data communications.

The present invention has been described in terms of the preferred embodiment, and it is recognized that equivalents, alternatives, and modifications, aside from those expressly stated, are possible and, within the scope of the appending claims.

What is claimed is:

1. A method for remotely managing an institution comprising the steps of:
   remotely collecting condition data representative of device status for a number of devices utilized in an institution, the condition data segregated into device diagnostic data and device reminder data;
   storing the condition data on a database at a centralized facility;
   reviewing the condition data to identify at least the device diagnostic data and the device reminder data; and
   separately displaying and identifying on a graphical user interface (GUI) the device diagnostic data and the device reminder data.

2. The method of claim 1 further comprising the step of automatically updating the GUI on one of user refreshing and user accessing of the GUI.

3. The method of claim 1 further comprising the step of indicating on the GUI the devices requiring immediate attention including identifying the devices in need of repair, servicing, and updating.

4. The method of claim 1 further comprising the step of displaying on the GUI a reminder profile including a list of devices that require routine attention.

5. The method of claim 1 wherein the institution is a medical institution and further comprising the step of displaying on the GUI news updates relating to the devices in the medical institutions.

6. The method of claim 5 further comprising the step of displaying news links to a number of news GUIs configured to display information about one of a device, a device technology, and a device development.

7. The method of claim 1 further comprising the step of identifying on the GUI a device location within the medical institution and further comprising the step of displaying on the GUI one of a department and an individual responsible for immediate management and monitoring of the device.

8. The method of claim 1 further comprising the step of displaying on the GUI billing information for a device.

9. The method of claim 1 wherein the device diagnostic data includes alert data requiring immediate operator attention and the device reminder data includes reminder data for eventual operator attention.

10. A graphical user interface (GUI) for a remotely located host configured to display management information for a plurality of devices comprising:
    an alert section having a number of alert indicators configured to indicate urgent items relating to a device;
    a reminder section having a number of reminder indicators configured to display scheduled items relating to the device; and
    a general information section having a number of general information textlinks configured to display product updates and technology news specific to the device.

11. The GUI of claim 10 wherein the number of alert indicators, the number of reminder indicators, and the number of general information textlinks automatically update with each user access.

12. The GUI of claim 10 wherein the number of alert indicators, the number of reminder indicators, and the number of general information textlinks are tailored to be specific to a particular user.

13. The GUI of claim 10 wherein a number of the alert indicators, a number of the reminder indicators, and a number of general information textlinks are further configured to link a user upon selection to a number of information specific GUIs.

14. The GUI of claim 10 configured to be accessed via an Internet connection.

15. The GUI of claim 10 further comprising a number of host navigational tabs including a "Services Home" tab, a "Solution Services" tab, a "Services" tab, an "Asset Management" tab, a "Financial Services" tab, an "Education" tab, and a "Contact Device Provider" tab, wherein the number of navigational tabs are configured to link a user to a number of service GUIs.

16. The GUI of claim 10 further configured to display a consolidation of automatically generated data and manually generated data including marketing data, customer-entered data, and messages from services and sales personnel.

17. The GUI of claim 10 wherein the host includes a medical institution.

18. A system to display consolidation information for a remote medical facility comprising;
    a computerized network;
    a readable memory electronically linked to the network;
    a plurality of computers connected to the network wherein at least one of the plurality of computers displays electronic data to a user in the form of a graphical user interface (GUI);
    a processing unit capable of calling a GUI on demand and causing a representation of condition data of a medical facility to be displayed upon request by a user;
    a plurality of devices in a remote medical facility connected to a consolidation facility; and
    a computer at the consolidation facility programmed to:
      continually acquire condition data of the plurality of devices;
      continually acquire reminder data wherein the reminder data includes a plurality of scheduled tasks;
      display the condition data and the reminder data on a refreshable graphical user interface (GUI); and
      enable data transmission to the remote medical facility in addition to the display of the condition data and the reminder data on the refreshable GUI.

19. The system of claim 18 wherein the computer is further programmed to determine a number of devices in need of immediate attention.

20. The system of claim 18 wherein the computer is further programmed to automatically display on the GUI updated condition data and the reminder data with each user access of the GUI.

21. The system of claim 18 wherein the computer is further programmed to automatically consolidate data from a number of auto-generation systems and manual generation systems including marketing messaging information, messages from remote personnel, and customer input information, and display the consolidated data on the GUI.

22. The system of claim 21 wherein the auto-generation systems include remote monitoring and diagnostic systems, network monitoring systems, dynamic asset tracking systems, billing, invoicing, and control management systems, and news providing systems.

23. The system of claim 18 wherein the computer is further programmed to acquire the condition data and the reminder data via a LAN, a WAN, a telephone system, a cable communication system, and a wireless system.

24. The system of claim 18 wherein the computer is further programmed to display on the GUI general information including industry news, device news, technology news, and news relating to the remote facility.

25. The system of claim 18 wherein the remote facility is a medical institution and the plurality of devices include medical diagnostic and medical imaging devices.

26. The system of claim 18 wherein the computer is further programmed to enable data transmission to allow information to be provided to the plurality of devices in the remote medical facility.

27. The system of claim 26 wherein the computer is further programmed to receive manually entered data and enable data transmission to allow information to be provided to the plurality of devices in the remote medical facility in response to receiving the manually entered data.

* * * * *

UNITED STATES PATENT AND TRADEMARK OFFICE
CERTIFICATE OF CORRECTION

PATENT NO.       : 7,774,211 B1                                                   Page 1 of 1
APPLICATION NO.  : 09/681475
DATED            : August 10, 2010
INVENTOR(S)      : Mullen et al.

It is certified that error appears in the above-identified patent and that said Letters Patent is hereby corrected as shown below:

Title Page, (75) Inventor, delete "Mobit S" and substitute therefore -- Mohit S. --.

Signed and Sealed this

Twenty-sixth Day of October, 2010

David J. Kappos
*Director of the United States Patent and Trademark Office*